(12) United States Patent
Hendriks et al.

(10) Patent No.: US 6,906,803 B2
(45) Date of Patent: Jun. 14, 2005

(54) INSPECTION OF SURFACES

(75) Inventors: Robert Frans Maria Hendriks, Eindhoven (NL); Teunis Willem Tukker, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 168 days.

(21) Appl. No.: 09/989,654

(22) Filed: Nov. 19, 2001

(65) Prior Publication Data

US 2002/0109848 A1 Aug. 15, 2002

(30) Foreign Application Priority Data

Nov. 20, 2000 (EP) .......................................... 00204103

(51) Int. Cl.[7] .................................................. G01B 9/02
(52) U.S. Cl. ...................................................... 356/484
(58) Field of Search ................................ 356/484, 485, 356/491, 492, 496, 511

(56) References Cited

U.S. PATENT DOCUMENTS 5,200,795 A  4/1993  Kim et al. .................. 356/345
6,084,671 A  * 7/2000  Holcomb ..................... 356/511
6,088,092 A  7/2000  Chen et al. ............... 356/237.2
6,122,058 A  * 9/2000  Van Der Werf et al. .... 356/635
6,151,127 A  * 11/2000  Kempe ........................ 356/484

FOREIGN PATENT DOCUMENTS

DE         4209701 A1     9/1993    ........... G01B/11/02
WO         WO9734124     9/1997    ............ G01C/9/02

OTHER PUBLICATIONS

Mueller, Guido et al. "Determination and optimization of mode matching into optical cavities by heterodyne detection". Optics Letters, Feb. 15, 2000, vol. 25, No. 4, pp. 266–268.*

* cited by examiner

Primary Examiner—Gregory J. Toatley, Jr.
Assistant Examiner—Michael A. Lyons
(74) Attorney, Agent, or Firm—Aaron Waxler

(57) ABSTRACT

A device for the inspection of surfaces, notably for the inspection of a surface of a semiconductor (14), which device comprises at least one laser light source (1) and a detector for detecting the light (13) that is reflected from the surface (10) to be inspected; the device also includes at least one mode filter (15; 15.1) for filtering the reflected light.

7 Claims, 4 Drawing Sheets

INSPECTION OF SURFACES

FIELD AND BACKGROUND OF THE INVENTION

The invention relates to a device for the inspection of surfaces as disclosed in the introductory part of claim 1, as well as to a mode filter as disclosed in the introductory part of claim 7, and to a method for the inspection of surfaces as disclosed in the introductory part of claim 9.

WO 97/34123 teaches the use of a laser for the inspection of surfaces where the light reflected by the surface is detected. When a defect occurs in or on the surface, the light applied to the surface by the laser light source is reflected in such a manner that at least a part of the light is scattered by the defect. The intensity thus decreases in the reflected component. Therefore, localization of defects is possible by measurement of the intensity of the reflected light. The resolution is limited and amounts to approximately 500 nm. Such a resolution, however, is not fine enough for the microstructures with conductor tracks or component groups that are situated very close to one another. Even when the scattered light that occurs at the defect is detected, the best sensitivity that can be achieved lies in the range of approximately 60 nm. In order to enhance the sensitivity, it would be necessary to reduce the irradiated region. However, the measurement would then become very time consuming.

SUMMARY OF THE INVENTION

It is an object of the invention to enhance the measurement of contaminations or damages on surfaces.

The construction of the device in accordance with the invention, where the light reflected by the surface traverses one or more mode filters, enables measurement of changes of the phase and/or of the amplitude of the reflected light relative to the applied light. Any reflection of light that exhibits a deviation in comparison with a reflection from an ideally smooth surface gives rise to such a change and hence can be detected. The sensitivity of a device in accordance with the invention, therefore, is significantly increased in comparison with said measurements of the absorption or the scatter. This enables the detection of defects of a size that amounts to only a quarter of the size that could be detected in conformity with the present state of the art. The mode filter also performs a spectral filtering of the light that is applied to the detector. As a result, a larger part of the scatter signal from air is suppressed. Notably the signal that is due to Brillouin scatter, being an inelastic scatter that, therefore, gives rise to a frequency shift of the scattered light relative to the applied light, is fully suppressed. Rayleigh scattering is also suppressed to some extent. Moreover, the signal strength is significantly increased: when glass having a refractive index of 1.5 is irradiated, the signal strength that is provided by the measuring method in accordance with the invention upon detection of a defect of a size of approximately 60 nm is approximately eight times higher than when a scatter signal is measured. When a silicon surface is irradiated, the signal strength is approximately 132 times as high. Moreover, the size of the detected defect can be determined on the basis of the change of mode, because the highest mode index $N_{max}$ that is still disturbed by a particle having a diameter d is proportional to $(1/d)^2$. It is also possible to preset a limit in respect of given defect sizes on the basis of appropriate modes. In methods that detect scattered light the signal strength is dependent on $(d/\lambda)^4$, where d is the size of a defect and $\lambda$ is the wavelength of the applied light. In the method in accordance with the invention the signal strength is proportional to $(d/\lambda)^2$. Consequently, as the defect is smaller, the rate of decrease of the signal strength will become far less than in the case of methods that detect scattered light, so that small defects can still be detected. This also enables a larger variation of the wavelength of the light.

In the case of a confocal measuring method, that is, a method where the detected region is situated in the focal point of an optical system that focuses the beam on the surface and where only this focal point is imaged in the detector, the disturbance that is due to the scattering on air is reduced to the near field of the focal point. A substantial part of the scatter from further layers of air is thus eliminated; the sensitivity of the measurement is thus significantly enhanced. Moreover, the scatter from optical elements that are not situated in a focusing plane is also removed from the measured signal.

When the mode filter removes the mode of the applied laser light, a so-called dark field measurement is performed. In that case a signal is received exclusively when a defect is measured on the surface. The signal-to-noise ratio is then better than in the case of a bright field measurement.

When the Guoy principle is applied to the mode filter, a mode is removed from a light beam containing a plurality of modes. For example, the mode of the laser can then be filtered out also in the case of reflected light that contains a mixture of modes.

As opposed to the detection of the intensity variation, scatter or phase delay on a defect as known thus far, the tracking of oscillation modes of the light in conformity with the invention provides a completely novel principle of measurement. When a defect is detected, the Gaussian eigenmode of the applied light does not occur in the light that is reflected from the surface, because a deviation from the ideal reflection occurs in the presence of a defect. This change can be detected.

Further advantages and details of the invention will become apparent from the following embodiments of the invention that are described with reference to the drawing.

DESCRIPTION OF THE PREFERRED EMBODIMENTS

Figure 1:
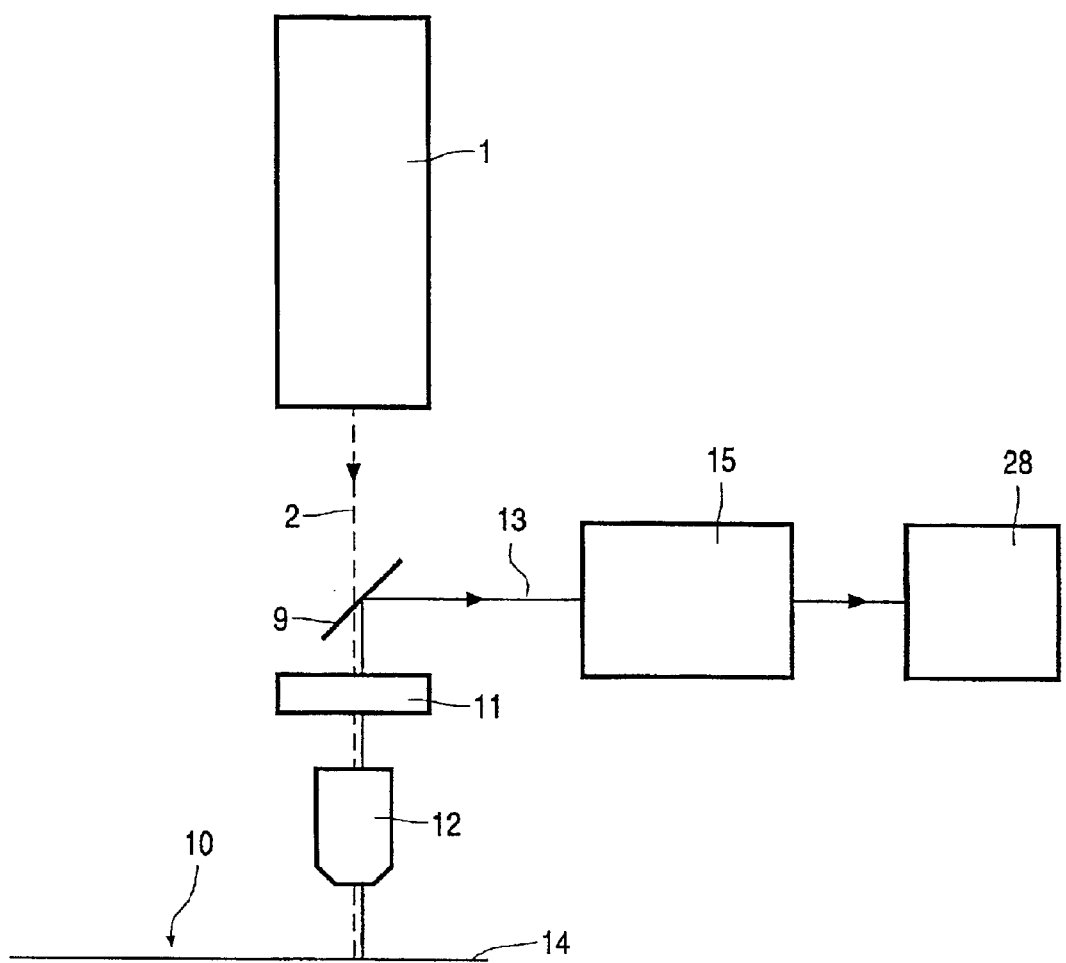
FIG. 1 is a diagrammatic representation of a first embodiment of the device.
Figure 2:
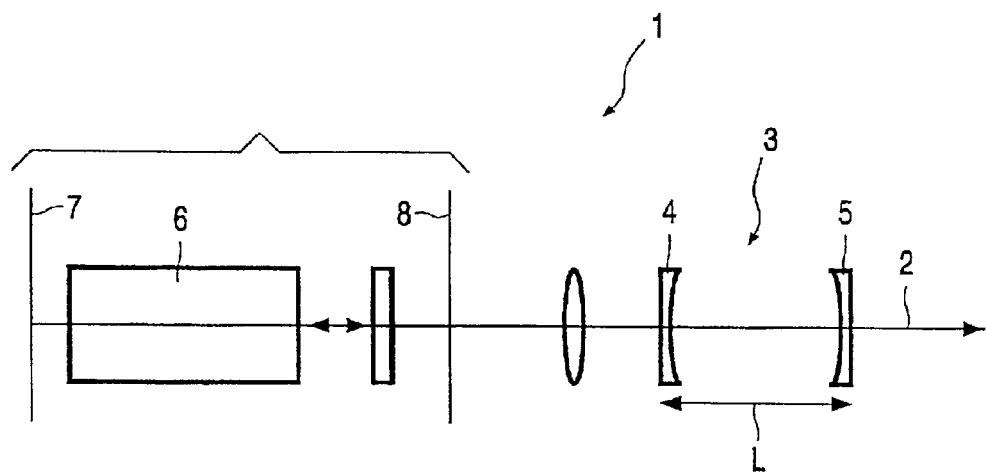
FIG. 2 is a diagrammatic detailed view of the laser light source.
Figure 5:
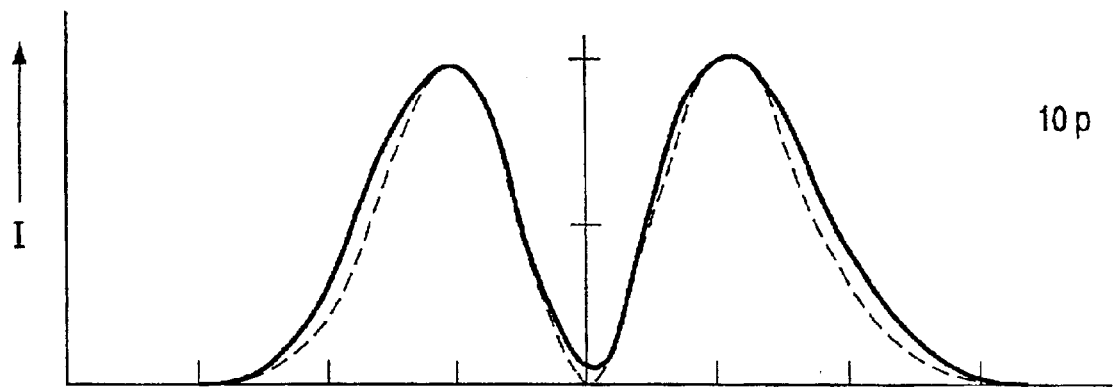
FIG. 5 is a diagrammatic representation of the $TEM_{10p}$ oscillation mode of the laser, viewed in the x direction.
Figure 6:
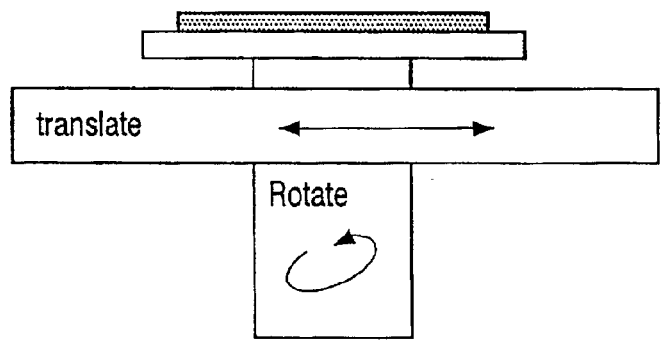
FIG. 6 is a diagrammatic view of the sample holder.

The embodiment of the device that is shown in FIG. 1 includes a light source 1 which is constructed as a laser light source and hence produces a high intensity. The laser light source 1 is provided with an optical resonator 3 which includes, for example mirrors 4, 5 that are adjustable relative to one another and are situated at a distance L from one another in the beam path of an emitted light beam 2. The mirrors 4, 5 are constructed as plane mirrors or as concave mirrors for ease of adjustment. Between these mirrors a standing wave is formed when the resonance condition is satisfied; this standing wave can be classified as a $TEM_{mnp}$, where the term TEM stands for transversal electromagnetic moment and the index m denotes the number of zero positions in the x direction, n is the number of zero positions in the y direction and p is the number of nodes along the length L of the resonator axis (of the order of magnitude of $10^6$ in the case of visible light and when the resonator has a length dimension of the order of magnitude of 10 cm). When the resonator 3 is adjusted, for example in such a manner that a mode $TEM_{10p}$ is realized, a zero-crossing occurs in the x direction in conformity with FIG. 5. Such a defined mode distribution of a laser is referred to as oscillation in a Gaussian eigenmode. When use is made of the resonator 3 that is shown, the laser light source 1, therefore, produces a light beam 2 in a single mode of oscillation. As is shown in FIG. 2, the resonator 3 may be connected so as to succeed the actual laser medium 6 that produces the light beam 2 by stimulated emission. In addition intra-cavity elements that enclose the laser medium are also arranged at that area; these elements already realize mode selection in the laser medium 6. The resonator 3 in that case serves as a downstream fine filter which ensures that only one mode indeed is contained in the beam 2 at the output side. It is alternatively possible for mirrors 7, 8 that enclose the laser medium 6, or other means that are directly associated with the laser medium 6, to act as a single resonator 3. The laser 1 operates continuously and delivers monochromatic light, for example, in the visible range; the light typically has, for example, a wavelength of 488 nm (argon laser). In principle various types of laser can be used, for example, solid-state lasers, semiconductor lasers or gas lasers. A titanium sapphire laser is used in the present embodiment.

Granted, use can be made of a light source with a reduced wavelength in order to improve the resolution, but the scatter cross-section of the light on the air enveloping the surface then increases. A measurement in a helium atmosphere or in vacuum conditions is also possible in theory, but is very expensive.

A beam splitter 9 is arranged in the beam path of the beam 2 emitted by the laser 1. The beam splitter may be constructed in various ways, for example as Fresnel's mirrors, as a double gap, as a combination of a polarizing optical cube and a λ/2 plate, or as another known mechanism. The present embodiment includes a semi-transparent, polarizing mirror 9 which is succeeded by a λ/4 plate 11 in the direction of the surface 10 to be inspected, which plate rotates the polarization plane of the applied light and produces elliptically polarized light at the output side; this light is incident at right angles, via a microscope objective 12, on the surface 10 of, for example, a wafer 14. In the case of an ideally smooth surface 10 it is ensured that the light 13 reflected thereby traverses the λ/4 plate 11 again and is deflected in the beam splitter 9 so as to be applied to the mode filter 15.

The use of a microscope objective 12 for focusing the light on the surface 10 enables a high accuracy to be achieved for the measuring method in accordance with the invention. Different microscope objectives 12 can be used in conformity with the desired resolution. The higher the accuracy, the longer the measurement will take, because the size of the light spot 9 on the surface 10 decreases.

Figure 7:
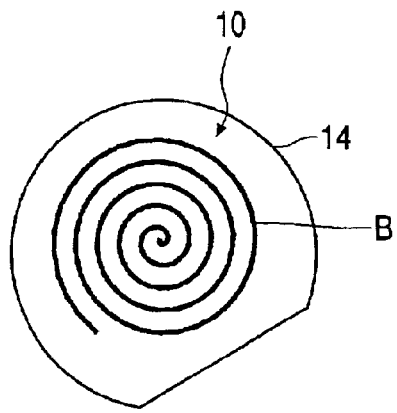
FIG. 7 is a plan view of the surface to be inspected in which the trajectory of motion is also shown.

The light spot 9 that is imaged on the surface 10 by the objective 12 can be moved by means of a movable optical system, that is, in the radial direction of the wafer 14 to be inspected in the present case, thus enabling complete scanning of the surface 10 thereof. The overall optical system that influences the incident beam 2 and must be very accurately adjusted with a view to the required accuracy can instead be very advantageously kept stationary while the wafer 14 performs, in addition to the rotary motion, a superposed translatory motion; this results in the spiral-like trajectory B of the object 14 that is shown in FIG. 7. The light spot retains its position and the wafer 14 is moved underneath the light spot in such a manner that its surface 10 can be completely scanned.

Various, partly known mode filters can be used as the mode filter 15. For example, either a further resonator or phase elements or optical fibers may be used.

Figure 3:
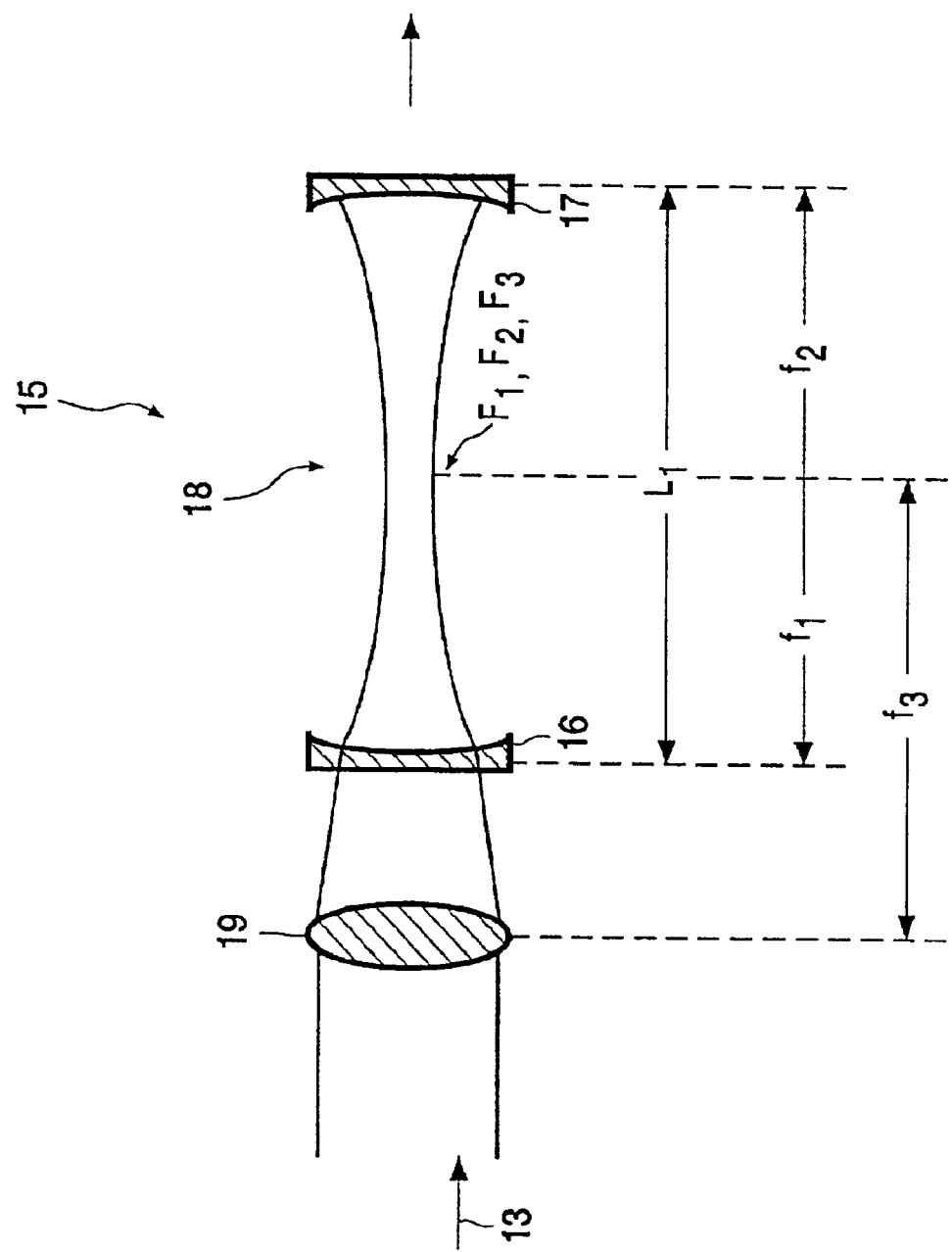
FIG. 3 is a diagrammatic view of a mode filter.

FIG. 3 shows a mode filter that is based on a resonator. Similar to the described resonator 3, two concave mirrors 16, 17 are provided therein as part of the laser light source 1; these mirrors are oriented perpendicularly to the optical axis and face one another. The incident light 13 enters, via the mirror 16, the resonator space 18 between the mirrors 16, 17 and is reflected by the rear mirror 17. The mirrors 16, 17 are situated at a distance $L_1$ from one another along the optical axis. This distance corresponds to the sum of the focal with f1 of the first mirror 16 and the focal width f2 of the second mirror 17. The focal widths f1 and f2 are the same in the embodiment shown in FIG. 3. However, this is not absolutely necessarily so. The distance between the mirrors 16, 17 and the focal width are dependent on the relevant mode to be suppressed in the resonator. The mode filter 15 in the beam path of the reflected light 13 is preceded by a collimating optical system 19, in this case being a converging lens whose focal width f3 corresponds to the sum of the distance between the lens 19 and the first mirror 16 and the focal width f1 of the first mirror 16. The focal points F1 and F2 of the mirrors 16, 17 and F3 of the lens 19, therefore, are situated at the same point in the present embodiment. This may vary in dependence on the desired mode that is to be suppressed. The parallel light 13 that enters the optical system is bundled in the focal point F3. Only the mode of the light 13 that satisfies the resonance conditions imposed by the curvature of the concave mirrors 16, 17 manages to pass through the mode filter 15.

Figure 4:
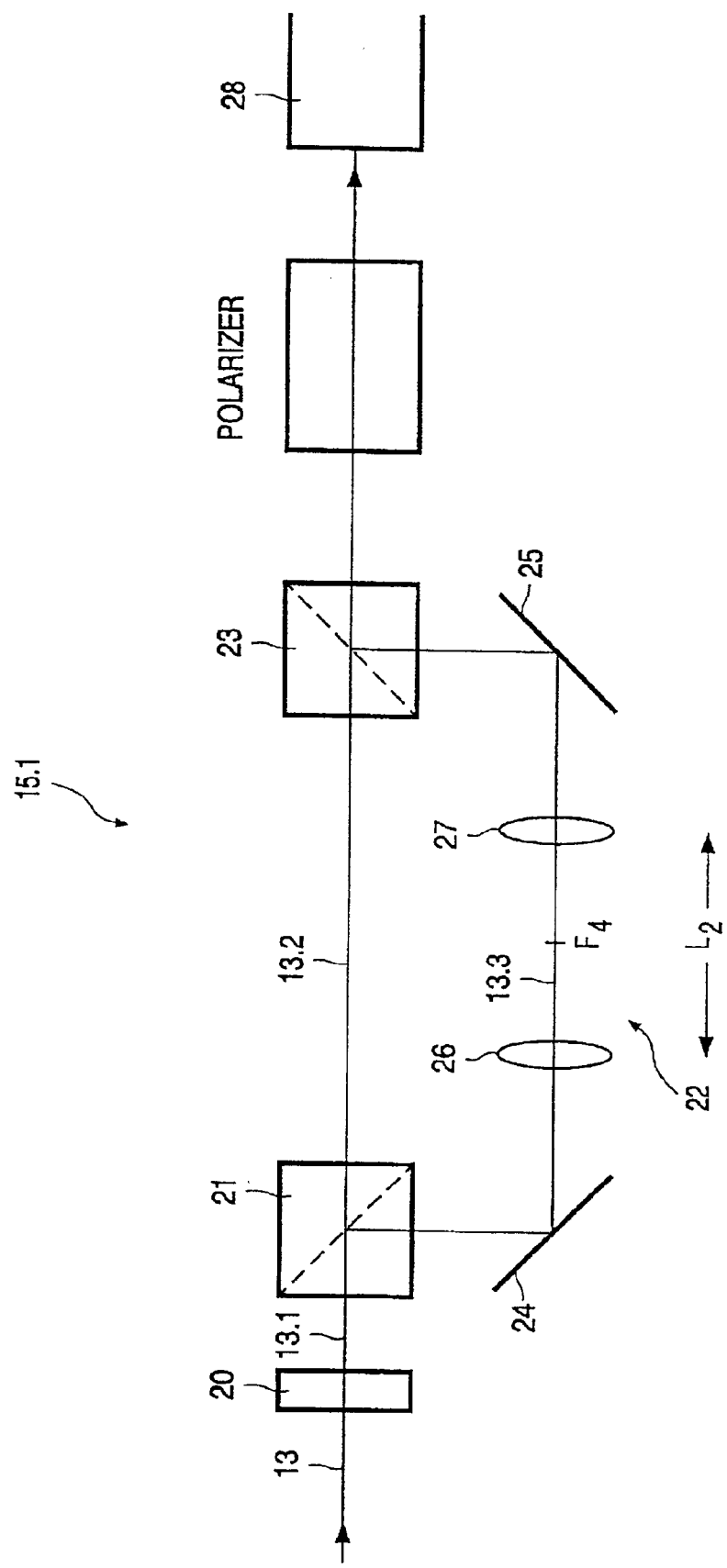
FIG. 4 is a diagrammatic view of an alternative mode filter.

FIG. 4 shows an alternative mode filter 15.1 whose overall construction resembles that of a Mach-Zehndner interferometer; therein the incident beam 13, which may contain a mixture of various modes, first traverses a λ/2 plate 20. The polarization plane of the incident beam is thus rotated through 90°.

The light beam 13.1 thus influenced is incident on a first polarizing beam splitter 21 which splits the beam 13.1 into the sub-beams 13.2 and 13.3, the sub-beam 13.2 being applied rectilinearly to a second beam splitter 23 in which the beams 13.2 and 13.3 are recombined.

The sub-beam 13.3 is deflected at right angles and is applied, via two mirrors 24 and 25, to the beam splitter 23 so as to be recombined with the first sub-beam 13.2. The sub-beam 13.3 has to travel a longer optical distance in comparison with the sub-beam 13.2. Between the mirrors 24 and 25 there is arranged a system of two lenses 26, 27 which are arranged at a distance $L_2$ from one another along the optical axis. This distance corresponds to twice the focal width of the lenses 26, 27 in the present embodiment.

The distance $L_2$ is adjusted exactly for the mode of the laser light source; this means that the light in this mode is subject to a phase shift in the focal point F4. When the phase difference between the sub-beams 13.2, 13.3 amounts to exactly 180°, the sub-beams 13.2 and 13.3 interfere, in as far as they oscillate exactly in this mode, destructively on the beam splitter 23. The phase difference is formed from the phase shift on the lenses 26, 27 and the difference in path length between the sub-beams 13.2 and 13.3. In the case of ideal reflection from the surface 10, that is, reflection without a change of the phase profile and the amplitude profile of the incident beam 2, therefore, no signal is received by the detector 28 that succeeds the mode filter 15 (dark field measurement). Consequently, disturbances have less effect on the measured signal than in the case of a bright field measurement.

The described phase shift of a mode between two lenses (Guoy phase) is proposed for the first time for a mode filter. Such a mode filter 15.1, however, may also be used for various applications of mode filters other than for surface inspection. A mode filter 15.1 is thus realized that reliably separates one mode whereas other modes are controlled to constructive interference. Various modes can be separated in dependence on the distance and the focal width of the lenses 26 and 27. The mode filter 15 can thus be tuned by variation of the lenses 26, 27.

The detector 28 need not operate in a space resolved manner, because the spatial resolution is provided by adjustment of the beam 2 that is incident on the surface 10. Various devices that convert the photons that enter into electrical signals are suitable for use as a detector, for example, secondary electron multipliers. Because such devices are very sensitive to light, very weak scattering of light can also be detected.

It will be evident that the light source 1, the surface 10 and the detector 28 can be arranged in a variety of ways that can be realized by selection of suitable deflection and converging optical systems. It is not necessary either, of course, that the light 2 is incident on the surface 10 from above; it may also enter from below or be oriented in a different way.

Typical parameters of the measurements are estimated on the basis of the following Table:

| 1) Signal strength: | |
| --- | --- |
| Signal strength | $I_t = 10^{-4}$ W |
| Highest mode index | $N_{max} = 1100$ |
| Highest non-disturbed mode | $M_{max} = 8$ |
| Detected signal | $\eta I_t = 7 * 10^{-7}$ W |
| 2) Light scattering: | |
| Effective density of the scattering layer of air | $\pi z_R = 5 \,\mu$W |
| Signal scattered back by air | $I_{air} = 5 * 10^{-11}$ W |
| 3) Mode filter: | |
| Suppression | $F^{-1} = 2.5 * 10^{-7}$ |
| Spectral width (FWHM) | $2\Delta\nu_{half} = 20$ MHz |
| 4) Noise: | |
| Background strength | $\|r\|^2 I_0 F^{-1} = 10^{-7}$ W |
| Background noise (rms) | $\Delta I_{rms} = 10^{-9}$ W |
| 5) Measuring speed: | |
| Measuring time per surface | $T_{waf} = 1$ h |
| Speed of rotation of the wafer | $\Omega/2\pi = 2000$ rpm |

The signal-to-noise ratio (SNR) for these parameters is approximately 700. Because this value is proportional to the fifth power of the defect size, a particle having a size of 16 nm can still be detected in the case of SNR=1.

It is to be noted that the device in accordance with the invention is not only suitable for the inspection of wafers 14, but also of arbitrary other semiconductor surfaces or other surfaces, for example substrates with thin layers, surfaces of optical or magnetic storage media, CDs, DVDs, and masks for the application of semiconductor structures, etc.

What is claimed is:

1. A device for the inspection of surfaces (10) of one or more semiconductors (14), comprising:

at least one laser light source (1);

a detector (28) for detecting an intensity of light (13) that is reflected by the surface (10) to be inspected; and at least one mode filter (15; 15.1) between the surface (10) and the detector (28); wherein the mode filter (15; 15.1) suppresses a mode in the reflected light (13) that corresponds to a mode of the laser light source (1).

2. A device according to claim 1, wherein the mode filter comprises a beam splitter (21) which splits a light beam (13) into at least two sub-beams (13.2; 13.3) that interfere with one another.

3. A device according to claim 2, wherein the mode filter includes a device (22) for mode-selective phase shifting and one of the sub-beams (13.3) traverses the device (22) for mode-selective phase shifting.

4. A device according to claim 3, wherein the device (22) effects a phase shift of a mode through 180° overall, together with a difference in path length, so that the sub-beams (13.2; 13.3) interfere destructively in respect of this mode.

5. A device according to claim 4, wherein the device (22) includes a lens system (26; 27) that operates on a Guoy phase system basis so as to effect the phase shift through 180°.

6. A method for the inspection of a surface of one or more semiconductors, comprising the steps of:

irradiating said surface by means of at least one laser light source; and detecting an intensity of light that is reflected by the surface to be inspected in at least one detector, wherein the laser light source emits light of a defined mode and that light that is reflected by the surface is guided through a mode filter.

7. A method according to claim 6, wherein the mode filter suppresses the mode of the laser light source and no signal is detected where reflection does not affect the mode.

* * * * *